United States Patent [19]

Birbara

[11] Patent Number: 5,894,608
[45] Date of Patent: Apr. 20, 1999

[54] PORTABLE SYSTEM FOR THE COLLECTION OF URINE

[76] Inventor: Philip J. Birbara, 404 E. 79th St., New York, N.Y. 10021

[21] Appl. No.: 08/933,385

[22] Filed: Sep. 19, 1997

Related U.S. Application Data

[63] Continuation-in-part of application No. 08/600,641, Feb. 13, 1996, abandoned.

[51] Int. Cl.⁶ ............................................. A47K 11/00
[52] U.S. Cl. ..................... 4/144.3; 4/144.4; 604/319; 604/355
[58] Field of Search ......................... 4/144.1, 144.3, 4/144.4; 604/73, 317, 319–321, 329, 331, 347, 318, 323, 326, 355, 327

[56] References Cited

U.S. PATENT DOCUMENTS

| | | | |
|---|---|---|---|
| 2,968,046 | 1/1961 | Duke | 4/144.3 |
| 3,114,916 | 12/1963 | Hadley | 4/144.3 |
| 3,757,356 | 9/1973 | Freeman . | |
| 4,270,539 | 6/1981 | Michaud . | |
| 4,275,731 | 6/1981 | Nichols | 604/319 |
| 4,281,655 | 8/1981 | Terauchi . | |
| 4,360,933 | 11/1982 | Kimura et al. | 4/144.1 X |
| 4,531,939 | 7/1985 | Izumi . | |
| 4,631,061 | 12/1986 | Martin | 604/323 X |
| 4,747,166 | 5/1988 | Kuntz | 4/144.1 |
| 4,904,248 | 2/1990 | Vaillancourt . | |
| 4,963,134 | 10/1990 | Backschneider et al. | 604/319 |
| 5,002,541 | 3/1991 | Conkling et al. . | |
| 5,053,027 | 10/1991 | Manfredi . | |
| 5,195,957 | 3/1993 | Carns . | |
| 5,230,164 | 7/1993 | Kishi | 4/111.1 |

FOREIGN PATENT DOCUMENTS

| | | | |
|---|---|---|---|
| 8600573 | 10/1987 | Netherlands . | |
| 2050838 | 1/1981 | United Kingdom . | |
| 2062472 | 5/1981 | United Kingdom | 4/144.1 |

Primary Examiner—J. Casimer Jacyna
Assistant Examiner—Kathleen J. Prunner
Attorney, Agent, or Firm—Birch, Stewart, Kolasch & Birch, LLP

[57] ABSTRACT

This invention relates to a compact, fully portable processing system for collection, sterilization, deodorization and eventual disposal of urine. The system is comprised of several detachable components which include male and female urine receptacles, an electric motor and fan assembly or any other suction source for providing the forced air flow required for urine entrainment; and a liquid collection bottle or reservoir. Optional but desirable features may include a gas/liquid separation or demisting element and a deodorizing filter. The system is self contained and readily disassembled for easy cleaning. It is readily adapted for home, hospital, and automobile usage. This invention has utility wherever rest room facilities are not conveniently available or where individuals are bedridden or immobilized.

10 Claims, 8 Drawing Sheets

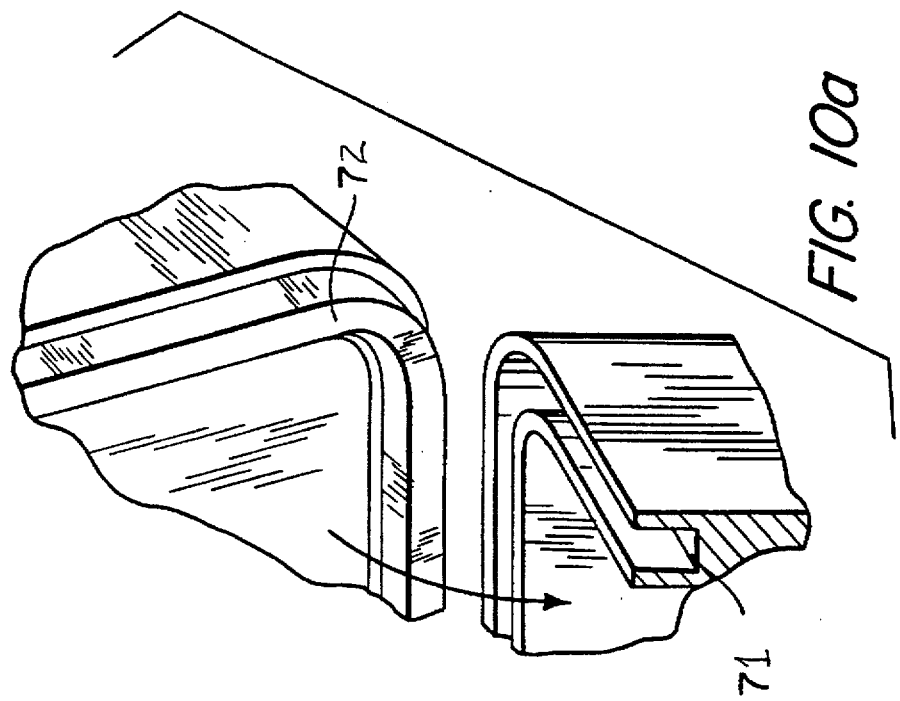
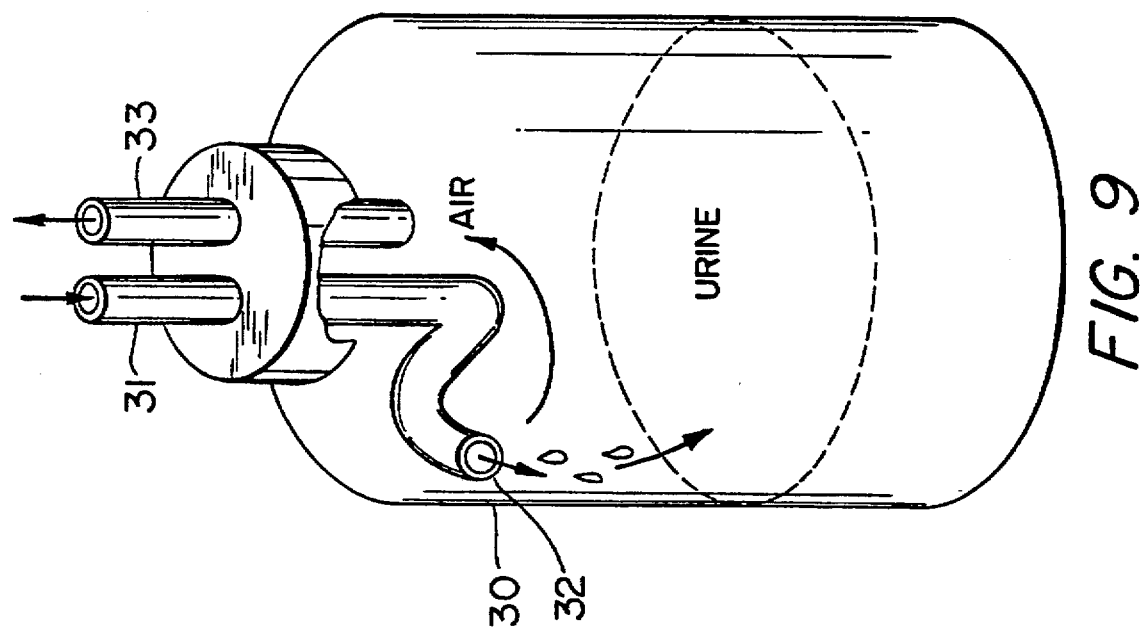

PORTABLE SYSTEM FOR THE COLLECTION OF URINE

CROSS-REFERENCES TO RELATED APPLICATIONS

A continuation-in-part of A PORTABLE SYSTEM FOR THE COLLECTION OF URINE (Ser. No. 08/600,641), filed Feb. 13, 1996 and now abandoned.

BACKGROUND OF THE INVENTION

1. Field of the Invention

This invention relates to a compact, fully portable processing system for the collection, sterilization, deodorization and eventual disposal of urine. Entrainment by a forced air stream is utilized to convey urine from the user in an arbitrary position—standing, sitting or prone to a suitable collection container.

2. Description of the Prior Art

The collection of urine is a process that has been extensively studied in conjunction with bedridden and incontinent individuals. Bed pans, diapers and/or catherization devices are generally utilized for those confined to beds for reasons of illness and disabilities. All of these practices have their drawbacks in view of suitable comfort and sanitary practices. Bed pan positioning is often difficult and urine collection is often not complete. Diapers are time consuming to attach and are costly. Furthermore, continued usage often leads to skin rashes, chaffing discomfort and potential infections. Catherization devices are most often prescribed for incontinent individuals. However, catherization devices run the risk of infection that can lead to undesirable side effects requiring medications and additional hospitalization confinement.

The prior art describes a variety of devices and processes to facilitate the withdrawal of urine from the body and disposal of the withdrawn urine. U.S. Pat. Nos. 4,270,539, 4,904,248 and 5,053,027 identify a variety of non-invasive devices that are worn and supported either by waist belts or held in place by supporting underwear garments. These devices are dependent on gravity for urine drainage into a collection bag, and therefore do not allow a user position where the urethra is not physically higher than the collection device. A urine aspiration system for the management of urinary incontinence is described in U.S. Pat. No. 4,747,166. Urine is collected in an absorbent pad which is connected to a vacuum source to remove urine from the pad to a collection container. The hydrophobic nature of the pad's cover contacting the body facilitates drying of the body surface in contact with the device within a short time period. The disposable pad must be changed frequently to satisfy sanitary concerns and to maintain the pad's absorptive capacity and sanitary properties.

U.S. Pat. No. 3,757,359 describes a therapeutic bed pan that is situated within the top surface of a mattress. The pan is covered with a perforated cover to permit urine collection within the pan. A vacuum source is activated to drain the bed pan to a collection vessel for eventual disposal.

Vacuum suction devices are described by the prior art. U.S. Pat. No. 2,968,046 discloses a urine receptacle which is emptied by the vacuum from an aspirating water jet. The aspirated stream of urine and air mixes with the water jet and is discharged into a drainpipe. However, the teaching is useful only where a user has access to a plumbed water system with provision for an aspirator system emptying into a drain, and cannot be considered "portable." U.S. Pat. No. 3,114,916 identifies a urinal system containing a cup shaped receptacle, a suction source as separate entities. U.S. Pat. No. 4,360,933 is similar in concept to U.S. Pat. No. 3,114,916; however, the suction source and collection container are described as separate entities that are connected with appropriate plumbing lines within a common housing. U.S. Pat. No. 4,360,933 describes an anti-spill feature that is effective only if the suction source is not active. U.S. Pat. No. 4,531,939 describes a similar system whose suction source is activated by a urine detecting element.

U.S. Pat. Nos. 2,968,046 and 3,114,916, 4,360,933 and 4,531,939 which rely on suction means for urine transport, disclose a variety of receptacle configurations, suction sources and collection containers. The prior art does not disclose a means for minimizing leakage at the body/receptacle interface and the importance of forced air entrainment at the base (lower contact end) of the receptacle. Several of the prior art practices as noted in U.S. Pat. Nos. 4,281,655, 4,631,061, 5,002,541 and 5,195,997 result in urine contacting the body prior to its conveyance to a remote collection container. Means for disengaging the fine urine droplets from a relatively high velocity air flow and removing urine related odors in the effluent air discharged to the surroundings are not addressed. Furthermore, the suction and collection means are not contained within a compact single assembly.

There exists a need for placing an orifice at the lower end of the receptacle in physical contact with the user to admit a wiping entrainment air to remove urine which might otherwise remain against the users or spill. It is functionally important that the ratio of air-to-urine flow be high. This facilitates drying the skin which has been in contact with the urine and more efficiently transports urine to the collection container so that fewer (if any) urine solids or salts are left behind to irritate the skin. A high air-to-urine flow ratio also requires a more efficient means for urine disengagement and demisting such as is taught by this disclosure.

There currently exist limited portable and self-contained urine collection systems for use within the inside of confined automotive interiors. The need for portable and self-contained urine collection hardware for travel usage is particularly desirable in situations where limited rest room facilities or long auto confinements are encountered.

The need for improved urine collection techniques for bedridden or incontinent people takes on an added importance due to an increasing elderly population, a greater dependence on home care and nursing home confinements and all situations where movement away from the bed is burdensome.

What is needed in the art is a compact and self-contained system which facilitates urine collection, sterilization, deodorization and eventual disposal in a sanitary and non-invasive manner for those who are bedridden, immobilized or where rest room facilities are not conveniently available for those confined to automobiles. It is an object of the present invention to satisfy these needs by providing for a leak-free urine collection device which prevents the carry-over of fine droplets of urine and removes urine related odors with minimal discomfort regardless of whether the user is in an upright, seated or prone orientation. The teachings of this invention are believed to be a distinct improvement over prior art devices.

SUMMARY OF THE INVENTION

This invention discloses a compact, portable processing system for collecting urine by forced air entrainment. The admission of entrainment air at the lowest point of a receptacle permits efficient and sanitary collection of urine from individuals whether they are situated in an upright, seated or a prone position. A method of collecting urine from a user into a portable and self-contained system consisting of:

a. activating a suction fan or other vacuum device to cause an aspirating flow of ambient air through openings or orifices on the sides of the receptacle with at least one of the openings located at the receptacle's lowest point in close proximity to the user-'s body;
   b. contacting the body with the receptacle which provides the necessary suction to seal against the body;
   c. entraining urine by an air stream at a high air-to-urine flow ratio to transport the urine to a remote collection container;
   d. separating the entrained urine from the air stream utilizing suitable inertial effects; and,
   e. collecting the separated urine liquid phase within a suitable container prior to its eventual disposal.

In a second aspect of the present invention, urine mist or droplets can be more effectively eliminated from the entrainment air stream by:

a. discharging the entrained urine into a cyclone element that is situated above the collection container such that the heavier liquid stream is forced to an inside surface which facilitates separation with liquid drainage to the bottom of the container while entrainment air is expelled to the suction source; or
   b. impinging the air and urine mixture against an inside surface of the collection container in a direction tangential to the plane of the container's wall to permit resulting centrifugal forces to separate the heavier liquid phase from the entrainment air.

Utilization of the cyclone element which is positioned above the collection container such that the separated urine enters the container at its geometric centroid results in the containment of urine even if the collection system is inadvertently knocked over providing the collected urine is less than one half of the container's capacity.

The receptacle's interfacial surface seal is non-invasive. In the case of the female user, the receptacle is configured to seal about the periphery of the vaginal opening. For male users, it is not required that the receptacle seal against the body, but the male receptacle may be configured to receive a directed urine effluent flow where the urine is entrained and transported to a remote collection container by air flow produced by a vacuum source or fan. On the other hand, for seated or prone male users, it is generally desirable that the receptacle seat against the user's skin. In this case, the seal is accomplished by the slight vacuum produced by the fan and the entrainment air flow which is admitted through one or several openings or orifices in close proximity to the body. A cylindrical or elliptical conical receptacle structure will also function to contain the urine effluent from male users.

A charcoal air filter impregnated with an acid such as phosphoric acid or acid salt such as potassium bisulfate may be placed either downstream of the point where urine is separated from the entraining air flow to remove ammoniacal or other urine odors prior to releasing the separated entrainment air to the surroundings.

The collected urine may be treated by bactericidal/deodorizing chemicals to disinfect and prevent the growth of microbial agents in the collected urine. Such chemical formulations might include but are not limited to citric acid, hydrogen peroxide solutions, potassium and/or sodium bisulfate, potassium persulfate, and sodium hypochlorite. Chemically treated urine can then be transferred to a waste disposal location at the user's convenience.

A pump and spray device may be provided to supply an appropriate flush solution and/or disinfectant rinse to facilitate the removal of urine residuals and contaminants from internal tubing and containment surfaces.

In another aspect of the present invention, an apparatus is provided for the collecting and eventual disposing of urine from the user's body. The basic elements of the portable, self-contained apparatus include:

a. a urine receptacle with a concave elliptical opening with a smooth interface surface at one end and a reduced cylindrical opening at the opposite end such that one or several openings or orifices penetrate the receptacle's wall to accommodate the inflow of entraining air where at least one of the openings is located at the lowest end of the receptacle that contacts the body;
   b. a liquid collection container which can serve to separate air and liquid and to contain the liquid; and,
   c. a fan or vacuum source to provide the air flow required to entrain and transport the urine from the user to the liquid collection container and to provide the suction needed to form a leak tight interfacial seal with the user's body.

By virtue of the practices of the present invention, methods and apparatus for the collecting and disposing of urine in a sanitary and non-invasive manner are described. The foregoing and other features and advantages of the present invention will become more apparent from the following description.

BRIEF DESCRIPTION OF THE DRAWINGS

As shown in FIG. 1, the right side of the receptacle cavity is positioned below the receptacle's outlet end.

FIG. 3 shows a perspective and side view of a receptacle configuration for male users while

FIG. 9 shows an alternative scheme for liquid/air separation where entrained urine and air mixtures are separated by centrifugal forces created by the tangential entry of the high velocity mixed air urine stream impacting the inner wall surface of the collection container.

FIG. 10a shows sealing details between the upper and lower portions of this portable unit.

DETAILED DESCRIPTION OF THE INVENTION

Figure 2:
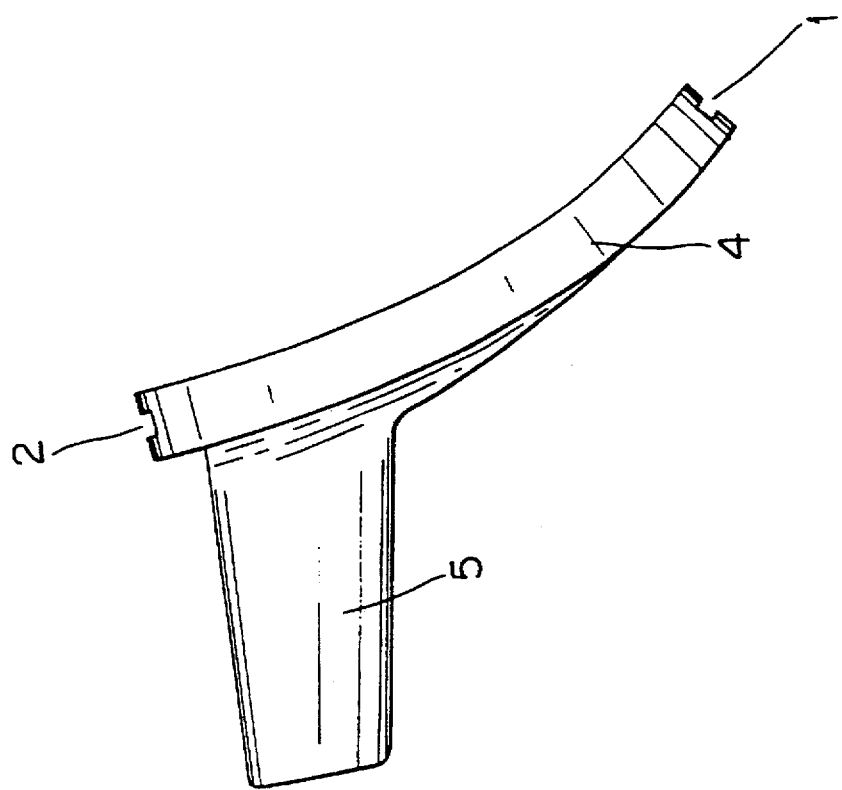
FIG. 2 is a side view of the urine receiving receptacle noted in FIG. 1.
Figure 1:
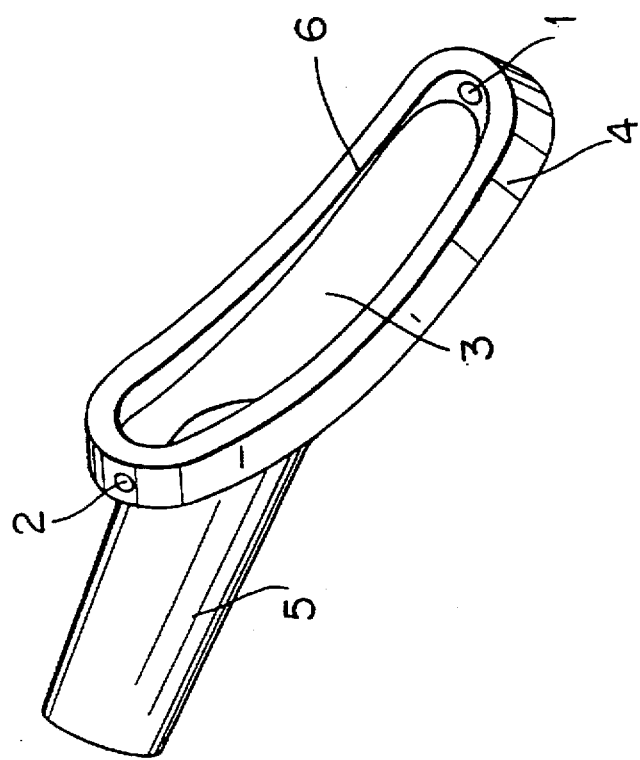
FIG. 1 is a perspective view looking into the receptacle which collects urine from a female user for transport to the collection container. The receptacle is placed in a position surrounding the urethra. Urine leakage from the subject is prevented by the suction created by a remote fan or other vacuum source connected to the ejection leg of the collection container. Urine is entrained by a high influent air flow entering the receptacle's bottom or lower and side or upper orifices which air flow transports the urine to the liquid collection container.

The present invention will be described in greater detail with regard to the processing system for the removal and collection of urine from the body. The design of a concave urine collector for receiving the flow of urine is an essential component of the processing system. Common structural design features of the urine collector(s) shown in FIGS. 1–5 which are unique to the present invention and are important for the comfort and convenience of the user are itemized as follows:

(a) The geometry and rigidity of the receptacle: For user comfort and to enable an air-tight seal between the user and the receptacle during use, the collector periphery must be sufficiently rigid that the user's skin is pressed into a conforming contour by the (partial) vacuum in the collector during use, but not so rigid as to be uncomfortable.

(b) The size and location of the entrainment air orifices: At least one or more orifices adjacent the sealing surface where at least one of the orifices is located at the bottom or lowest end of the collector to admit entrainment air to effectively entrain the urine entering the receptacle into a flowing air stream. This entrainment air also serves to dry the skin and prevent an inadvertent spillage when the device is removed. These orifices must be located at- or close to- the periphery of the receptacle within approximately 0–10 mm and preferably 0–4 mm of the user's skin. These orifices must also be of sufficient number and size to enable a aspirating air velocity of approximately 10–30 ft/sec or more adjacent to the skin area encompassed by the receptacle which might otherwise be wet by urine. It should be apparent from the geometric configurations shown in FIGS. 1–5 that the lower air entrainment port at the bottom or lowermost portion of the receptacle is the most important, and preferably the entrainment air port at the bottom or lowermost portion of the receptacle should be the largest and admit the greatest amount of entrainment air.

(c) The line length and diameter leading to the evacuation port: In order to enable the uphill flow of the entrained urine such that the user will not be wet by his own urine regardless of the orientation of the device or of the user's body, an aspirating air velocity of approximately 40 ft/sec or more and a ratio of air-to-urine of approximately 50:1 (by volume) or more is required. Since a maximum urination rate of approximately 40 cc/sec is possible for some persons, the required air flow is about 2 liters/sec or about 4 cfm. A line to the suction source having an I.D. of at least ⅜ inches is desirable but preferably the line to the suction source should have an inside diameter of ½–⅝ inches.

The preferred configuration of the collector differs in form for females and males. For females as noted in FIGS. 1 and 2, the collector is shaped with a concave elliptical opening defined by outer rim 4 and sealing surface 6 which contacts the human body. Typically, the concave elliptical opening is 1 inch wide by about 4 inches long. Lower orifice 1 and upper orifice 2 at the lowest and highest ends of the collector, respectively, are located in the periphery of the elliptical collector which enable air at relatively high velocities, preferably about 20 to 50 feet per second to enter the collector. The effluent end 5 of the collector reduces to about ⅝ to ¾ inches I.D. within a length of approximately 3–4 inches. The elliptical and concave back surface 3 that faces the body is configured to increase in depth from about ¼–½ inches along the collector outer rim 4 adjacent lower orifice 1 to about 1 inch in depth where it intersects the effluent channel 5. The high air velocity associated with the shallow depth at the lower end of the receptacle is effective in entraining a urine liquid stream and drying the skin area which would otherwise be wet with urine.

Typically, the lower orifice 1 which may or may not be circular should have a cross-sectional area of about ⅛ in$^2$ while the upper orifice 2 has about ¼ of this area. The air flow, typically ranging from 2 to 15 cubic feet per minute, is effected by a fan located downstream of the urine collection container. The suction from the fan causes the collector's peripheral sealing surface 6 defined upon outer rim 4, typically about ⅛ inch to ¼ inch wide, to press against the skin to form a seal. By this means, the urine effluent from the body is confined and entrained by air flowing through the receptacle's orifices and into the connecting tube leading to the urine collection container. In practice, an air flow of about 4 ft$^3$/min will result in an air velocity of about 75 ft/sec through a ⅛ in$^2$ receptacle orifice area and a velocity of about 20 ft/sec through a ¾ inch diameter tube leading to the urine collection container.

Figure 3:
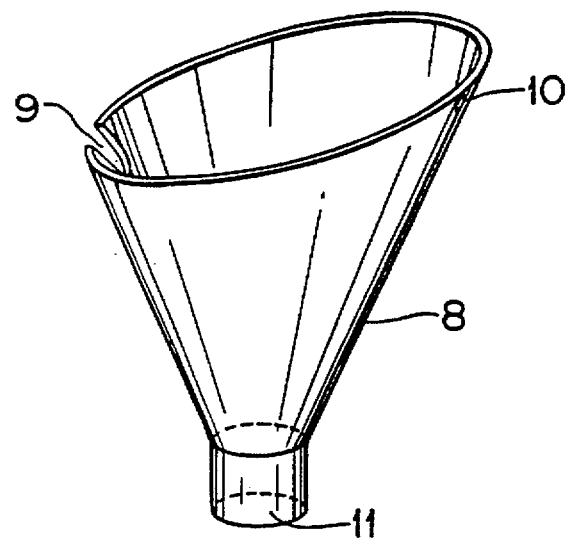

In FIG. 3, a typical male receptacle 8 can have a conventional conical shape with an inlet diameter typically from 2 to 3 inches and reduces to an outlet 11 having a diameter of about ⅝ inch. Alternatively, the male receptacle 8 may have an elliptical shape of about 5 inches long by 3 inches wide reducing to an outlet diameter 11 of about ⅝ inches. Lower orifice 9 at the lowest end of the collector rim is about ¼ inches in diameter while the upper orifice 10 is about ⅛ inches in diameter.

Figure 4:
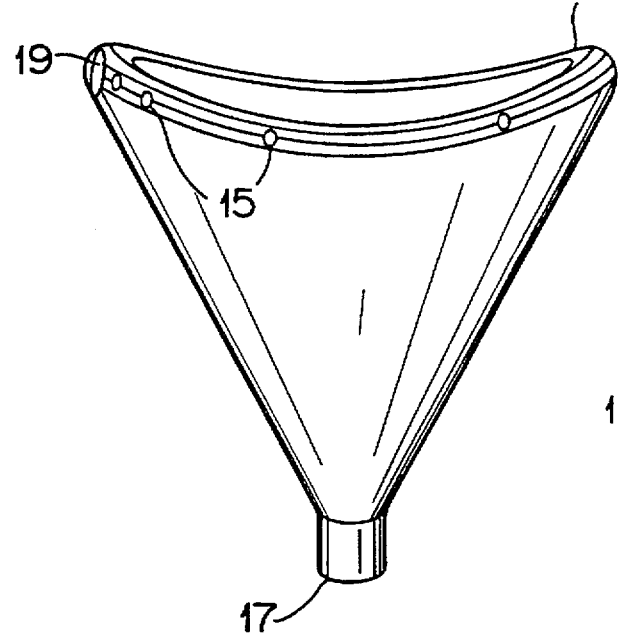
FIGS. 4 and 5 depict a perspective and cross-sectional view of a male/unisex receptacle.
Figure 5:
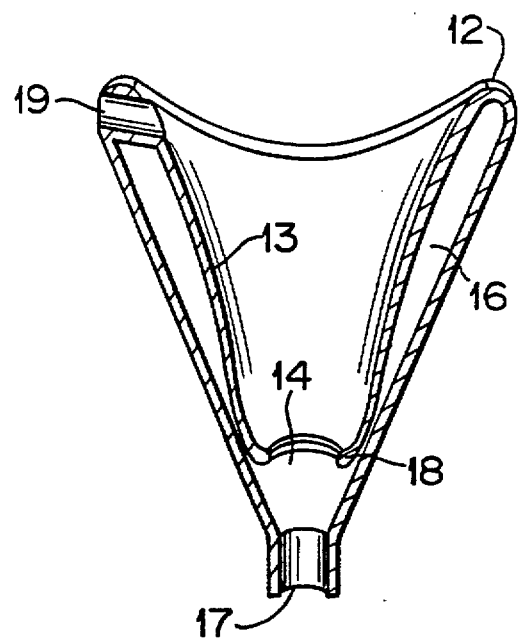

Another male or unisex receptacle 12 is shown in its isometric form and in its cross section in FIGS. 4 and 5. In these Figures, the elongated contour of the inner cone 13 allows efficient recovery of urine emitted from a male member even when it is inserted at an off-angle such that the urine stream is not aimed directly at the orifice 14. Preferably, it is fabricated from a soft hydrophobic plastic or elastomeric material which is not wet by the incoming urine stream. For unisex use, the circular rim defining the inlet region is easily deformed by finger pressure to an ovalized configuration more convenient and comfortable to a female user.

The device, shown in FIGS. 4 and 5, features a multiplicity of orifices 15 along the upper rim of receptacle 12 to admit inlet air to the manifold region 16. During use, the inlet air flows out from the manifold region 16 through the annular orifice 18 and through outlet 17 en route to a central vacuum source. Any urine passing through exhaust orifice 14 is entrained by this airflow and swept along to the central vacuum source where the urine is disengaged and separated from the air flow as discussed previously. Preferably, the total flow area comprised by the multiplicity of orifices 15 in the collector rim is several times greater than the annular flow area 18 defined between the inner and outer funnel shells such that the function of the device is not appreciably impaired if one or even a number of the inlet ports or orifices 15 should be blocked by direct contact with the skin or clothing of the user. However, it is also preferable that the outlet flow area 17 be comparable to the annular flow area 18 so that during use a sufficient vacuum is developed at 16 that any urine which may inadvertently not be aimed directly at orifice 14 will nevertheless be aspirated by an inflow of air past the user's member if there is an imperfect seal between the user's body and the outer rim of the receptacle, or if there is a perfect seal between the user's body and the outer rim of the receptacle, the urine will be aspirated upon withdrawal of the receptacle when the seal is broken. For the female user, it is most desirable that a sweeping air flow be admitted directly to the interior region 13 and 14 through a single large lower orifice 19 at the lowest point of the upper rim of receptacle 12. When utilized by a female user, the secondary air flow through lower orifice 19 dries and aspirates the wetness away from the users skin. To perform this function, lower orifice 19 should be sized such that it will admit about one-half of the total air aspirated through the exhaust port 17 when employed by a female user. It is most efficient if lower orifice 19 contacts the body at the lowest elevation so as to effectively transport urine to the collection chamber.

Figure 6:
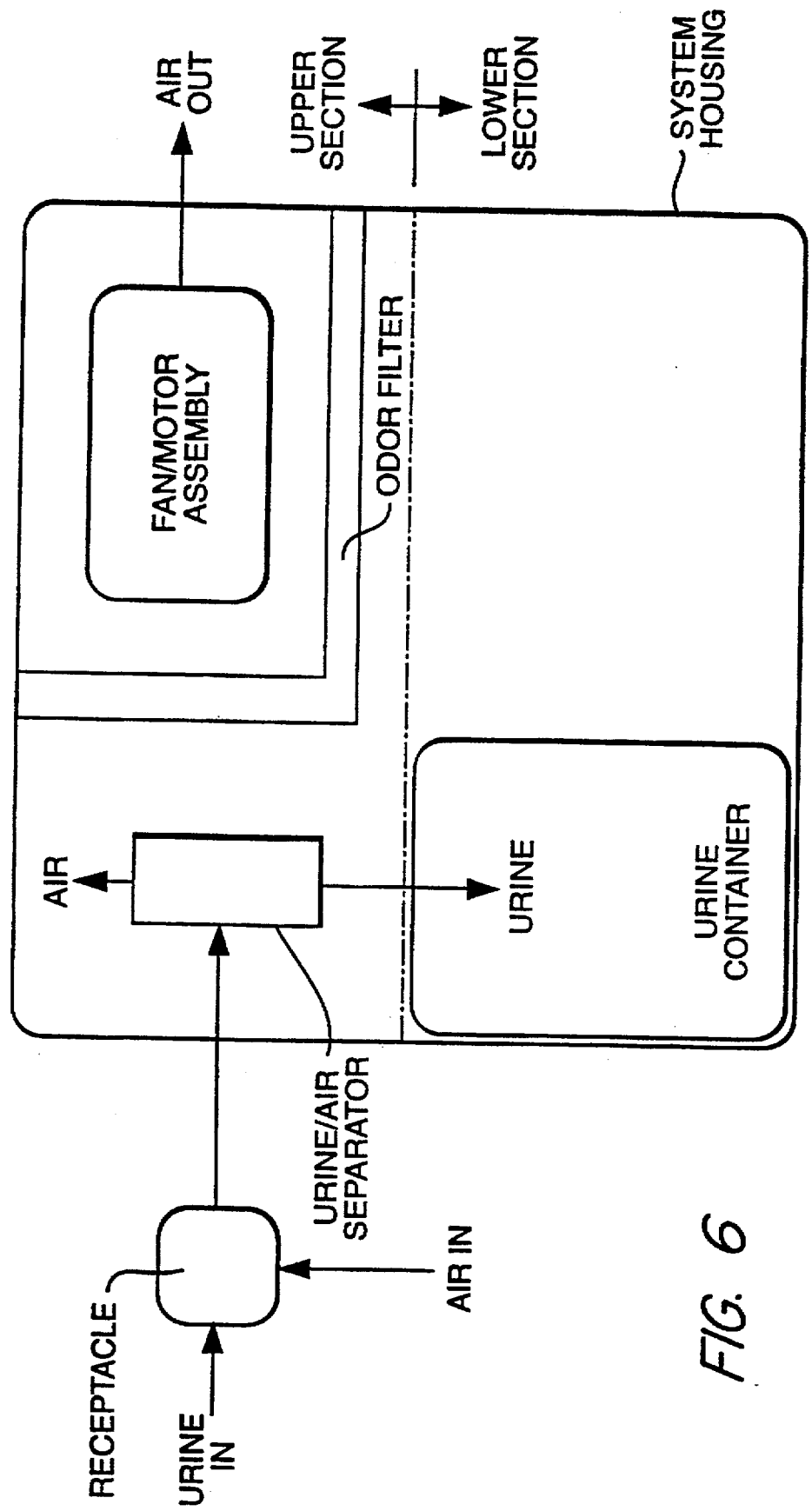
FIG. 6 is a flow typical outline schematic of the urine collection and disposal processing system.

Visual tests were conducted using a prototype device similar to that shown in the flow schematic illustrated in FIG. 6 with simulated urine stream. The fan assembly generated a static vacuum of about 10 inches of water. A female collector receptacle with a concave elliptical opening of 1 inch wide by 4 inches long was used for the tests. The receptacle featured lower and upper orifices having, respectively, cross-sectional areas of $\frac{1}{8}$ in$^2$ and $\frac{1}{32}$ in$^2$. These orifices were located at the bottom and top of the receptacle, respectively, to admit an entraining air flow into the system. The air with the entrained urine stream was conveyed through a ¾ inch diameter flexible transparent tube over a distance of 10 feet to a remote collection container. The simulated urine was composed of 5 wt % sodium chloride and 4 wt % urea dissolved in demineralized water. It should be noted that these salts comprise the major constituents of urine.

It was observed that the simulated urine flow was readily entrained by an air flow of 4 ft$^3$/min. The internal velocities through the receptacle and tubing were more than sufficient to transport all of the simulated urine to the collection container. Upon cessation of the simulated urine flow, an effective drying of a simulated body surface in contact with the receptacle was noted.

The urine collection container, configured as shown in FIGS. 6 and 8–11, efficiently separated the liquid urine from the air stream such that liquid was collected in the bottom of the collection container. The effluent air discharged from the top of the collection container was free of entrained liquid. Tests run with a 2 liter urine collection container having a diameter to height ratio of about 1:1 showed an effective separation of an air and a liquid stream with air flows of about 4 ft$^3$/min. Injection of the liquid and air mixture in a tangential direction on the upper portion of the container's inner surface, as noted in FIG. 9, was observed to enhance liquid/gas separation.

As noted in the process schematic of FIG. 6, a suction fan which creates the air flows necessary to entrain the urine must be situated downstream of the urine collection container. As a consequence of the fan's operation, the collection container is maintained at a vacuum of 6–10 inches of water during use.

An odor filter may be situated either upstream or downstream of the fan assembly, but it is preferably located upstream of the fan assembly to provide additional protection to the motor and fan against long term fouling from urine contaminants. The odor filter may consist of a high surface area carbon (about 1000 m$^2$/gm) impregnated with an acid salt and/or a weak acid to enhance removal of ammoniacal odors from the air flow. Testing has indicated that a contact residence time of about 0.05 to 0.5 seconds with 8–12 mesh activated carbon granules impregnated with a concentration of 10% phosphoric acid effectively removes residual urine odors.

Figure 8:
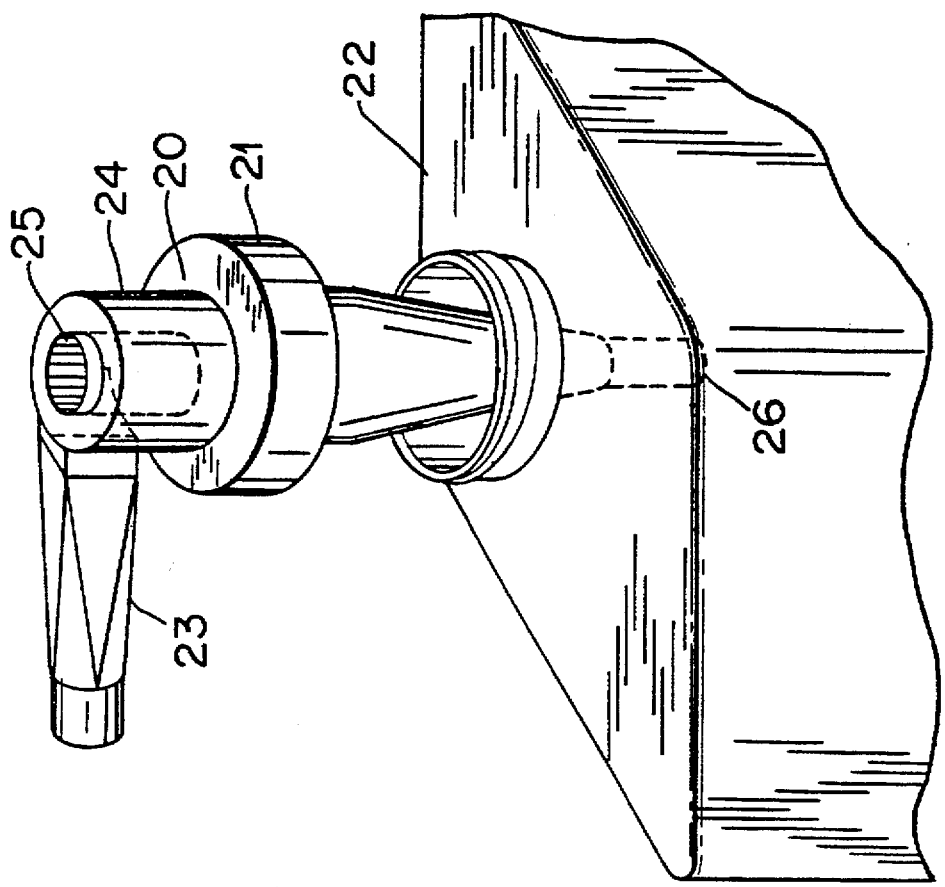
FIGS. 7 and 8 show details of a system liquid/air separation or demisting element where the urine is disengaged from the entraining air flow and allowed to enter the collection container. The configuration where the liquid outlet from separation element is positioned at or close to the geometric centroid of the collection container provides a measure of urine containment against inadvertent tipping of the portable collection system.
Figure 7:
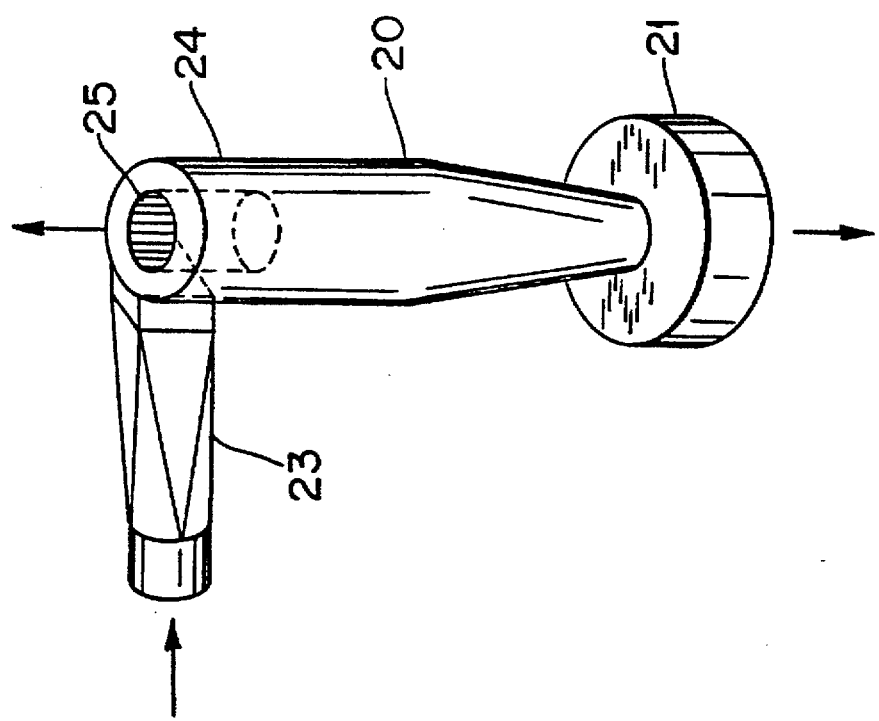

FIG. 7 depicts a typical cyclone separator unit 20 which is integrated with a cap 21 that screws into a collection container 22 shown in FIG. 8. The inlet 23 to the cyclone element 23 receives the entrained urine and air mixture from the receptacle assembly as noted in the process flow schematic of FIG. 6. This mixture enters the cyclone at the upper end of the cylindrical body 24 such that the incoming flow duct is tangential to the surface of wall 24 and is swirled rapidly by the confining geometry. The swirling, which may generate centrifugal forces ranging from 100–1000 gravities depending upon the velocity of the incoming urine/air mixture and the radius of the curvature of the cylindrical body 24, causes the liquid phase to be centrifuged to the outer wall whereupon it drains into the collection container 22. As shown in FIGS. 7 and 8, the separated air stream exhausts through a tubular upper port 25. Upper port 25 typically starts at a vertical plane immediately below the bottom of inlet tube 23 and extends approximately one-quarter of its diameter above the top of cylindrical body 24. Suction is maintained at this station by the action of the fan as shown in the schematic of FIG. 6.

In FIG. 8, a similar cyclone element 20 is also integrated with screw cap 21, but the position of the cyclone is such that the liquid outlet 26 is positioned at the geometric center or centroid of collection container 22. This arrangement achieves an anti-spill configuration; i.e., as long as the collection container 22 is less than one-half filled with liquid, the liquid outlet 26 of the cyclone element will always be above the liquid level whether the assembly should fall on its side, on its end, or even be turned upside down. It will be recognized by one trained in the art that this anti-spill configuration is effective only as long as the collection container 22 is less than half full of liquid and therefore the collection chamber typically should be oversized to approximately twice as great as the maximum intended liquid capacity.

FIG. 9 depicts an alternate configuration for the separation of urine from an entraining air stream. Inlet tube 31 is configured to impart a swirling velocity component to the outflow stream 32 within collection container 30. The swirl serves to separate the gas and liquid phases such that the liquid is centrifuged to the outer wall of collection container 30. Upon reaching the container's wall, the droplets and mist coalesce against the collection chamber wall and descend to the bottom of collection container 30 while the separated air stream flows radially inward and exits through exhaust tube 33 to a region of diminished pressure resulting from the suction source typically through a filter/deodorizing component as shown in FIG. 6.

Figure 10:
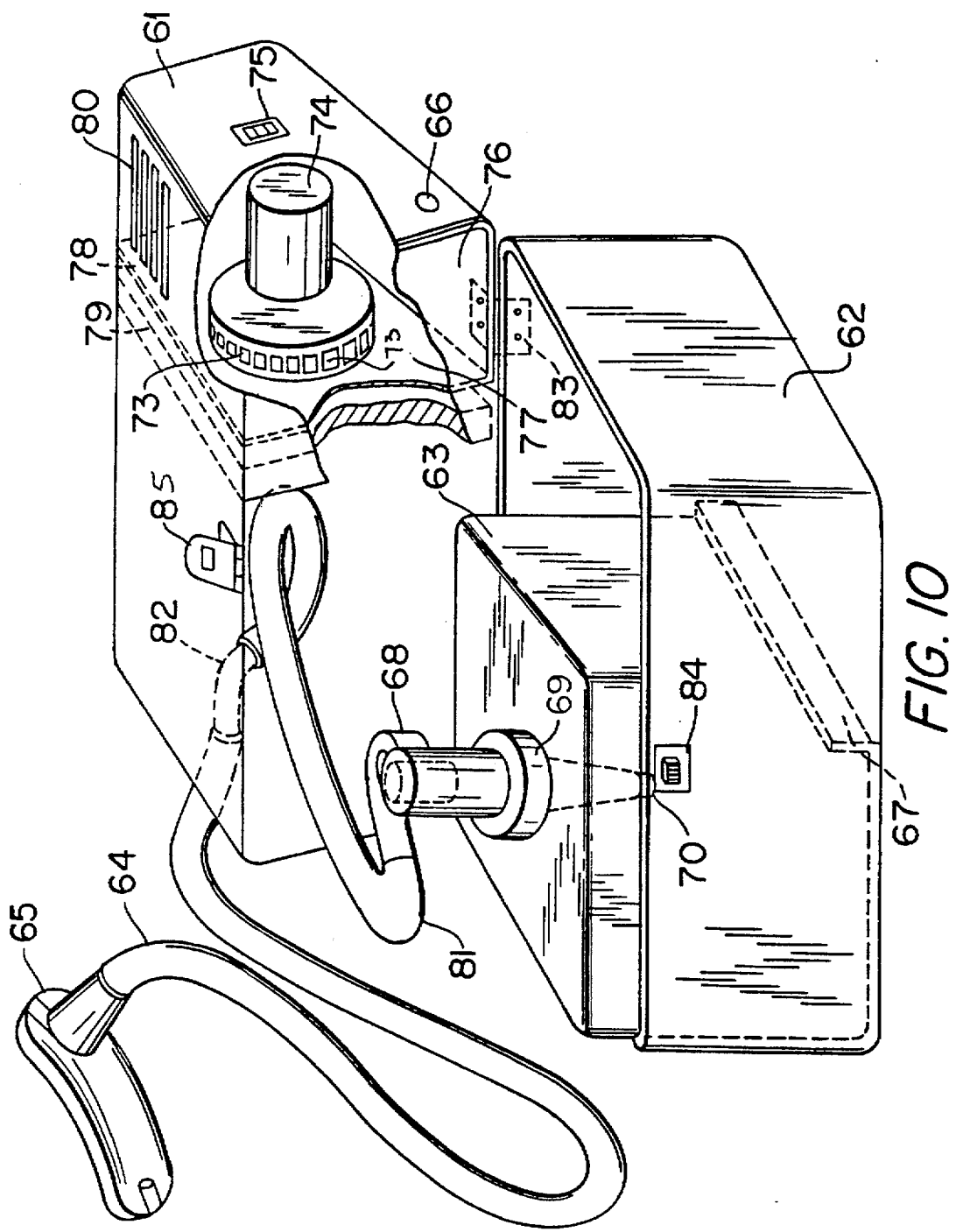
FIG. 10 shows a schematic of a portable embodiment of the invention configured into a compact envelope.

One embodiment of the urine collection system which is especially convenient for travel or wherever electrical power is available is shown in FIG. 10. In this Figure, the system is completely contained within a "lunch-box" sized container. The container is comprised of top 61 and bottom 62 halves. The bottom half contains a urine collection container 63 over approximately one half of its base area and provides storage volume for the collection hose 64, the male and female urine receptacles 65 and an electrical cable which can be plugged into jack 66 to power the fan 73. Within the bottom half of the container 62, an intermediate partition 67 segregates the urine collection container from the storage volume and restrains it against inadvertent tipping or tumbling within the container assembly.

A cyclone separator element 68 is held by a screw cap 69 at a vertical height such that liquid outlet 70 is at the geometric center of the collection container. This anti-spill design feature is functional as long as the container's liquid volume is less than one-half full. A hermetic sealing configuration between mating edges 71 and 72 (also shown in FIG. 10a) provides anti-spill redundancy and prevents the escape of odoriferous gases.

In the top half of the container, fan 73 is driven by an electric motor 74 which is activated by switch 75. The upper quarter volume containing the fan and motor assembly is partitioned off from the rest of the assembly by baseplate 76 and bulkhead 77. After urine/air separation, it can be seen that the recovered air is admitted from fan inlet region 78 to fan 73 only after passing through a deodorizing/demisting filter 79 into plenum 78 feeding the fan through a hole in bullhead 77. As shown in FIG. 10, the opening in bulkhead 77 is typically adjacent to the fan inlet and concentric with the fan centerline. To reach fan inlet region 78, air which has been separated from the air/urine inflow by cyclone element 68 flows through a deodorizing activated charcoal filter 79. This further suppresses odor and provides a second line of defense against urine escape. During use, the interior volume of the urine collection system is maintained at subambient pressure by the suction of the fan 73. Fan 73 also pumps the clean interior air back up to atmospheric pressure where it exhausts through ports or louvers 80. Typically, it may prove expedient to line the interior wall of the region containing fan 73 and motor 74 adjacent to exhaust ports 80 with an acoustical lining material but it should be apparent to one skilled in the art that this is a user convenience and is not essential to the system's operation.

In the design shown in FIG. 10, a tube fabricated from a flexible inert material such as Tygon™, conducts the incoming urine/air stream to cyclone separation element 68 while accommodating the opening, disassembly and cleaning of the device. The incoming urine and air stream are conveyed through the outer wall of the unit by a fitting 82 which connects to hose elements 64 and 81 on the exterior and interior regions of the urine collection system shown. Finally, a suitable latching mechanism or hinge 83 and latch elements 84 and 85 seal upper 61 and lower 62 halves of the urine collection system.

Figure 11:
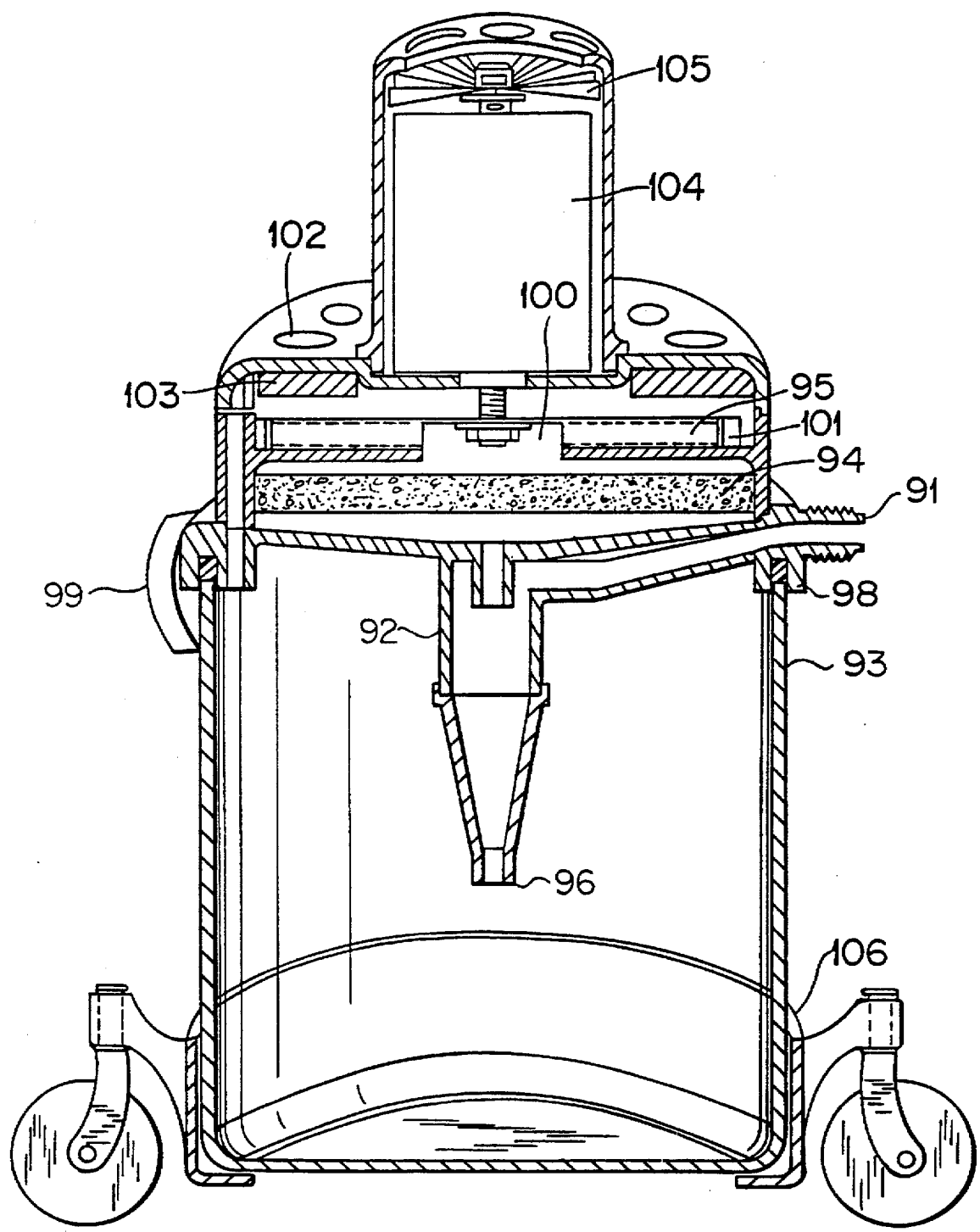
FIGS. 11 and 12 are schematics of a home or hospital embodiment of the invention.
Figure 12:
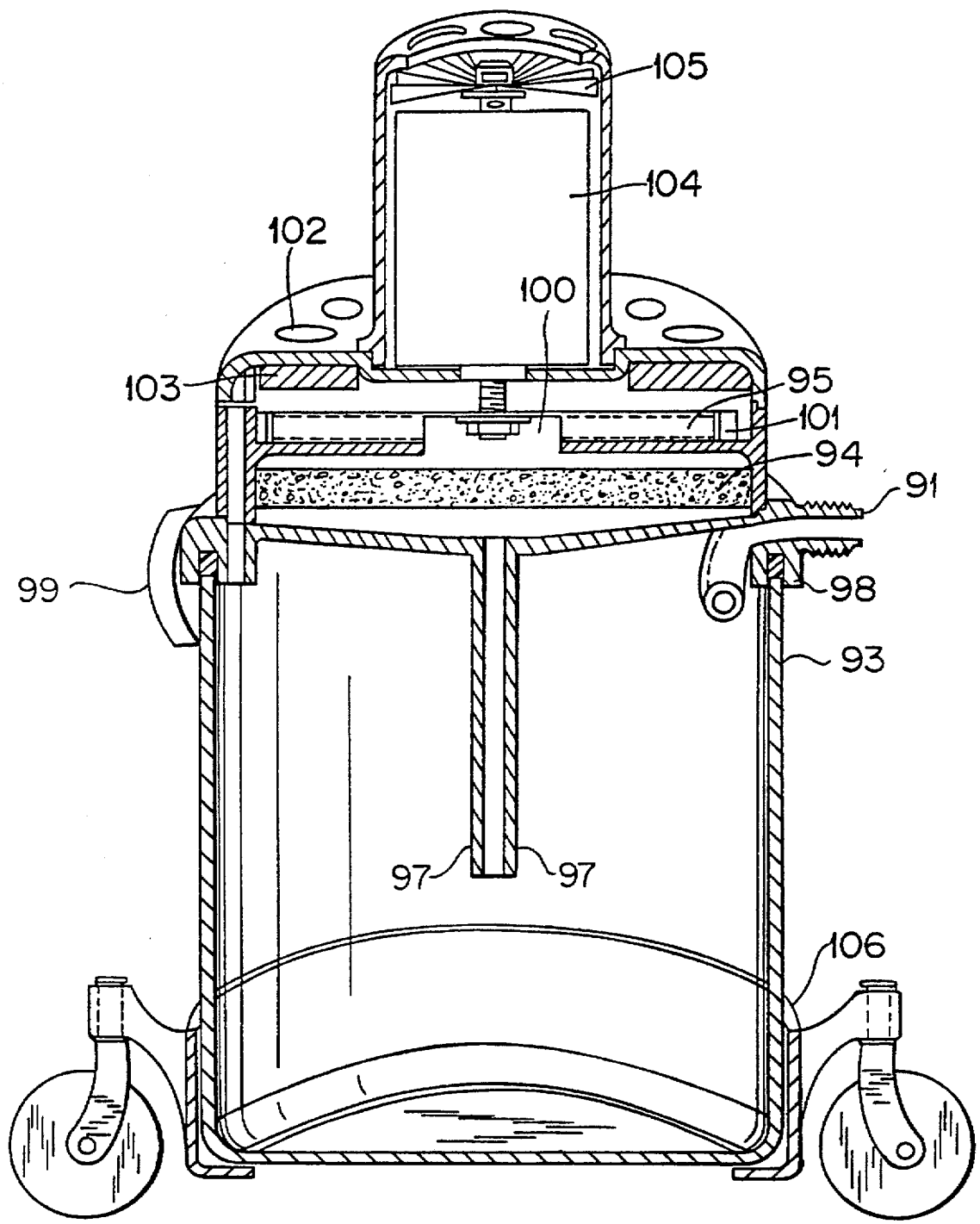

A home or hospital embodiment of the invention is shown in FIGS. 11 and 12. A urine/air mixture is aspirated through inlet port 91 where it flows directly into a cyclone separator 92 as shown in FIG. 11 or into a swirling jet which impacts the wall of liquid collection container 93 at a shallow angle as shown in FIG. 12. The combination of centrifugal and gravity forces separates gas and liquid phases. The liquid-free effluent gas stream flows up through an acid impregnated activated charcoal filter 94. Filter 94 deodorizes the effluent gas stream by removing ammoniacal contaminants prior to its recompression back to atmospheric pressure by fan element 95. It should be noted that anti-spill configurations are depicted in both FIGS. 11 and 12. The liquid discharge port 96 of cyclone separator 92 in FIG. 11 and the inlet of the gas exhaust tube 97 in FIG. 12 are both located at the geometric center of liquid collection container 93.

In FIGS. 11 and 12, seal ring 98 enables the motor/fan/separator assembly to form a hermetic seal with liquid collection container 93. The two halves of the assembly are closed by a multiplicity of hasps 99 which protect the user against unwelcome odors or from an inadvertent spill. The gas stream exiting from the impregnated charcoal filter 94 is admitted to the center 100 of rotating fan element 95 where it is swirled outward against stator elements 101 which recompresses the effluent air back up to atmospheric pressure. After pressure recovery, the deodorized air stream exits the apparatus through a multiplicity of exhaust ports 102 which may be downstream of an optional acoustic element 103 for noise reduction. As an element of good practice, it should be noted that the motor 104 which drives fan element 95 is desirably self cooled by an air stream which is separate from the primary aspirated air stream, and is drawn in by cooling air fan 105. Optionally, a home or hospital system may be configured with a dedicated trolley or cart 106 to facilitate its transport according to a user's convenience.

As will be apparent to those skilled in the art in the light of the foregoing disclosure, many substitutions, alterations and modifications such as the addition of a liquid sensing device to activate the suction source are possible in the practices of this invention without departing from the spirit or scope thereof.

I claim:

1. Apparatus for the collection and eventual disposal of urine from the human body, comprising:
   a. a concave urine collector having an elliptical outer rim with a sealing surface defining an upper end and a lower end and adapted for vertical orientation in use with the upper end above the lower end, the rim contacting the human body, said elliptical outer rim including a major axis and a minor axis, said urine collector including:
      i. one or more orifices adjacent the sealing surface where at least one of the orifices is a lower orifice located at the lower end of the collector to admit entrainment air, said at least one lower orifice is generally aligned with the major axis of the elliptical outer rim; and
      ii. an effluent channel leading away from the collector intermediate the upper end and the lower end;
   b. a flexible connection attached at one end to said urine collector effluent channel and including a free end leading away from the effluent channel, and operatively attached to a urine storage chamber;
   c. said urine storage chamber adapted to separate entrainment air and urine and to contain the urine; and
   d. an entrainment air fan adapted to entrain ambient air through said one or more orifices and said collector so as to transport urine to said urine storage chamber.

2. Apparatus for the collection and eventual disposal of urine from the human body as in claim 1, said urine collector being adapted for vertical orientation in contact with the human body, wherein said one or more orifices includes at least one upper orifice at the upper end of the collector.

3. Apparatus for collection and eventual disposal of urine from the human body as in claim 2, including a cyclone separator interposed between said storage chamber and said concave urine collector, so as to separate entrained urine from said flowing air.

4. Apparatus for collection and eventual disposal of urine as in claim 2, said urine storage chamber having a curved wall, such that entrained urine and flowing air is capable of being directed tangentially thereto.

5. Apparatus for the collection and eventual disposal of urine as in claim 2, wherein said entrainment air fan develops an aspirating air velocity of 10–30 ft/ sec.

6. Apparatus for the collection and eventual disposal of urine as in claim 5, wherein said entrainment air fan develops an entrainment air flow within the range of 2 to 15 cubic feet per minute.

7. The apparatus for the collection and eventual disposal of urine as in claim 2, wherein there is one of said at least one upper orifice, said one upper orifice is generally aligned with the major axis of the elliptical outer rim.

8. The apparatus for the collection and eventual disposal of urine as in claim 7, wherein said effluent channel is located adjacent said upper end, adjacent said upper orifice.

9. The apparatus for the collection and eventual disposal of urine as in claim 1, wherein said effluent channel is located adjacent said upper end.

10. The apparatus for the collection and eventual disposal of urine as in claim 9, wherein said effluent channel is generally aligned with the major axis of said elliptical outer rim, at a spaced location from said minor axis.

* * * * *